United States Patent [19]

Martinez

[11] 4,393,542
[45] Jul. 19, 1983

[54] POLYCENTRIC HINGE FOR CAST-BRACES

[76] Inventor: Gonzalo Martinez, P.O. Box 12304, Bogotá, Colombia

[21] Appl. No.: 170,485

[22] Filed: Jul. 21, 1980

[51] Int. Cl.³ .............................................. E05D 7/00
[52] U.S. Cl. ..................................................... 16/369
[58] Field of Search ............. 128/80 C, 80 R; 16/180, 16/368, 369

[56] References Cited

U.S. PATENT DOCUMENTS

| | | | |
|---|---|---|---|
| 2,587,166 | 2/1952 | Jovick | 128/80 C |
| 3,669,105 | 6/1972 | Castiglia | 128/80 C |
| 4,144,881 | 3/1979 | Chappell | 128/80 R |

FOREIGN PATENT DOCUMENTS

| | | | |
|---|---|---|---|
| 79821 | 1/1920 | Austria | 128/80 C |
| 1534434 | 12/1978 | United Kingdom | 128/80 C |

Primary Examiner—Werner H. Schroeder
Assistant Examiner—Andrew M. Falik
Attorney, Agent, or Firm—Ladas & Parry

[57] ABSTRACT

A hinge for a knee joint comprising two complimentary elements. One of said elements is a plurality of interconnected links. The links are interconnected in zig-zag manner. The other of said elements is a cable. The linkage and the cable are secured at the respective opposite ends to plates or like elongated elements.

3 Claims, 5 Drawing Figures

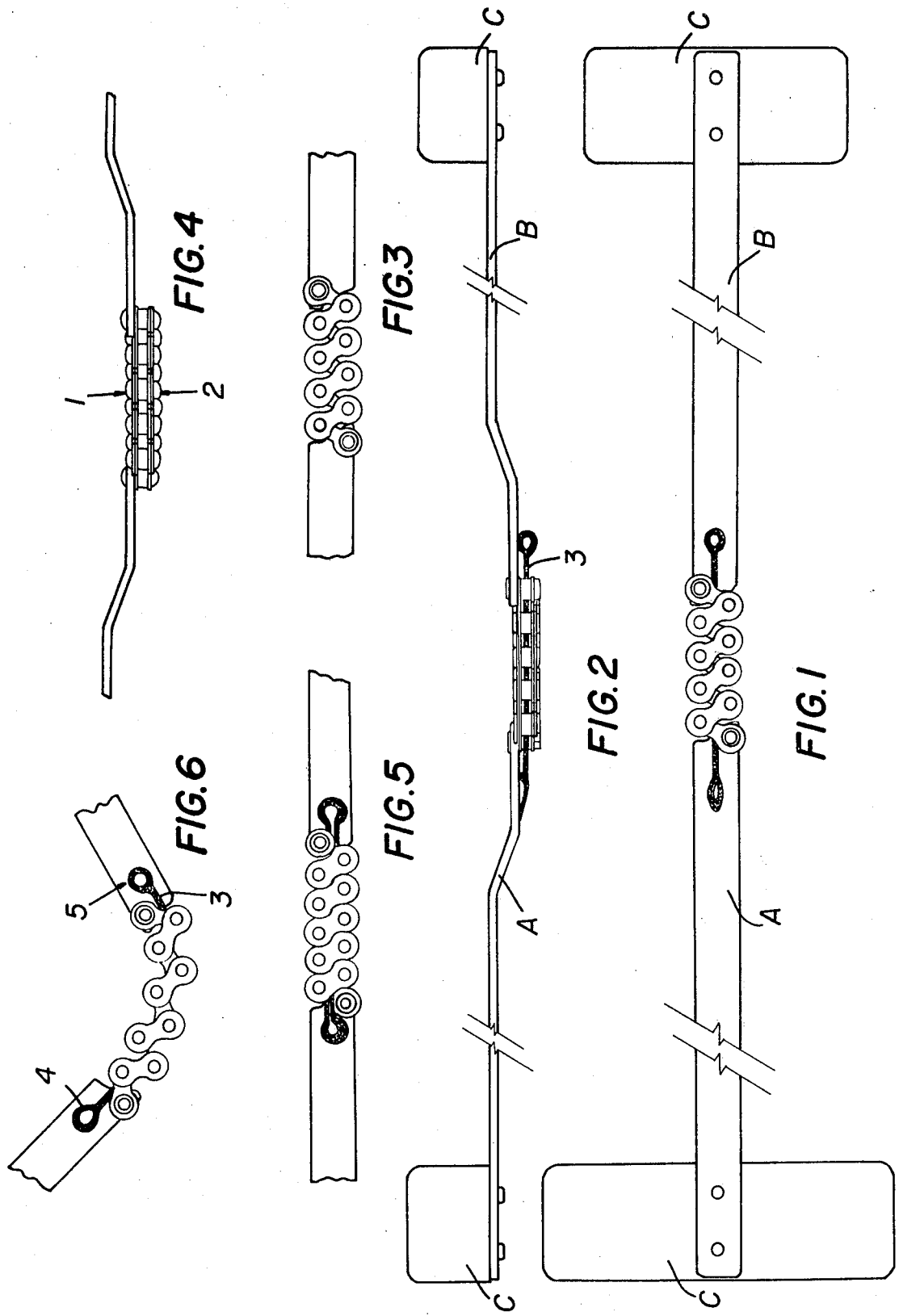

POLYCENTRIC HINGE FOR CAST-BRACES

The present invention relates to a polycentric hinge applicable for cast-braces of the knee joint.

In applying such cast braces, the ideal hinge mechanism should provide lateral stability and at the same time comply with the changing centers of flexion and tolerate a certain degree of rotation of the normal knee joint. A failure to fulfill these requirements causes a harmful stress on the joint cartilage and ligaments.

Hinges tried so far for cast braces have been:
(1) Unicentric hinges, which do not follow the instant centers of flexion of the knee.
(2) Bicentric hinges (with an intermediate link) which are satisfactory within a useful range, but only if they are centered and leveled very exactly and if the length of the intermediate link is adequate for the size of the patient. Both conditions are very difficult to apply in a normal practice.
(3) Wire or plastic links which are multicentric, but they cannot transmit rotatory movements from the leg to the thigh-part of the cast, or viceversa, which is one of the purposes of a brace cast in the knee joint. Wires also have the disadvantage of permitting distal slipping of the thigh part of the cast when standing.

As used in this specification, the term "sagital plane" depicts the vertical plane that passes through the human body parallel to the sagital suture and divides the body into left and right portions. The "coronal plane" is a frontal plane and divides the body into front and back portions.

The present invention is a hinge which is stable in the coronal plane, multicentric in the sagital plane, and offers no difficulty in centering it at the time of its application because of its compliance with any instant center of flexion in spite of the usual proximal or distal displacement of the hinge as it is being bound to the thigh and leg casts.

FIG. 1 shows front and plan elevations of a hinge of the invention

FIG. 2 shows a front elevation of a detail of FIG. 1

FIG. 3 shows a plan view of the detail shown in FIG. 2

FIG. 4 is a front elevation showing a further detail, and

FIG. 5 is a front view showing an expanded position.

Referring now to the drawing, FIG. 1 shows the complete assembly of the hinge, consisting of two flat metallic bars (A,B) 15 to 20 cm. long (for use according to individual patient's size). At the extremity, each bar has a wider plate (C) attached to it, about 15 cm.×4 cm. for the proximal (thigh) and about 10 cm.×4 cm. for the distal (leg) piece. The plates may or may not be perforated.

As described so far, there is no essential change comparing this brace with other braces used at the present time, and the same metals may be used in its construction.

FIG. 2 shows the hinge mechanism which links the two bars. It consists of a link belt similar to a bicycle chain in which the links have been arranged in a zig-zag manner. The size and metal of the chain is the same as that used for standard bicycle chains. There is no advantage in changing the dimensions of the standard bicycle chain as far as distance between centers of each link, thickness of plates and quality of steel are concerned. The standard bicycle chain, however, has a lateral tolerance which is inconvenient for the purposes of a cast-brace. Therefore, the rods which connect the links have a wide riveted head 1,2 on each side of the chain.

The chain so arranged in a zig-zag manner is easily disarranged unless a flexible steel or cable 3 is threaded through the space formed along the center of the zig-zag pattern, that is, between the two bolts of each individual link. Such a cable may be of an elastic material generally known as Sylastic.

If an elastic material is used for this purpose, it must have a wide head on each end to avoid its slipping off from the system. Such a wide head is most clearly shown in FIGS. 4 and 5. Steel cable, however, has a longer endurance. A 1.5 mm. to 2 mm. cable of 10 to 16 twisted steel filaments is quite sufficient. When steel cable is used the proximal end of it is soldered to a bar 4 and a spherical or drop-like head 5 is placed at the distal end of the cable, but not attached to the distal element, allowing the cable to slide within the zig-zag arrangement of the links and preventing the disarrangement of the zig-zag pattern.

A nine link chain is a good size hinge for the purposes of polycentric bending in an average size knee joint. Such a chain is particularly advantageous since it allows a wide enough margin of error in attaching the brace to the cast. Seven or five link systems work biomechanically very well, but are much less tolerant to error in their application.

The length of the cable, of course, depends on the number of links. Having the proximal end fixed to the bar, its distal head slides distally in extension and retracts within the chain in flexion. Thus, the distal head of the cable should touch the most distal link and make the cable tense beyond 90° of flexion.

The end links of the chain are best attached preferably rivetted, soldered or otherwise fixed to each bar because, unless both bar and chain are of steel upon articulation chafing or abrasion would soon cause the bar to wear out and the entire system would become loose and laterally unstable. However, with the end links fixed to the bars, iron, aluminum or any alloy cheaper than steel may be used for the bars.

I claim:

1. A hinge for a knee brace including an elongated element attachable to a leg above the knee and a further elongated element attachable to the leg below the knee, said element being interconnected by a multi-flexible linkage comprising individual links pivotally interconnected in zig-zag manner and a cable anchored at one end to one of said elongated elements and threaded through the zig-zag links.

2. A hinge according to claim 1, wherein the cable is threaded through a space extending centrally through zig-zag linkage.

3. A hinge according to claim 1, wherein one end of the cable is fixed with respect to its associated elongated element and the other end is slidably retained within the zig-zag arrangement of the links by a wide head attached to the end of the cable.

* * * * *